(12) United States Patent
Kamei et al.

(10) Patent No.: US 8,808,675 B2
(45) Date of Patent: Aug. 19, 2014

(54) ORGANOPOLYSILOXANE HAIR TREATMENT AGENT AND HAIR COSMETIC CONTAINING THE TREATMENT AGENT

(75) Inventors: Masanao Kamei, Gunma (JP); Kiyomi Tachibana, Tokyo (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 456 days.

(21) Appl. No.: 10/553,214

(22) PCT Filed: Apr. 14, 2003

(86) PCT No.: PCT/JP03/04705
§ 371 (c)(1),
(2), (4) Date: Oct. 13, 2005

(87) PCT Pub. No.: WO2004/091562
PCT Pub. Date: Oct. 28, 2004

(65) Prior Publication Data
US 2006/0210506 A1 Sep. 21, 2006

(51) Int. Cl.
*A61Q 5/12* (2006.01)
*A61K 8/894* (2006.01)
*A61K 8/898* (2006.01)

(52) U.S. Cl.
CPC . *A61K 8/894* (2013.01); *A61Q 5/12* (2013.01); *A61K 8/898* (2013.01)
USPC .................................. 424/70.12; 524/731

(58) Field of Classification Search
None
See application file for complete search history.

(56) References Cited

U.S. PATENT DOCUMENTS

| | | | | |
|---|---|---|---|---|
| 4,183,366 | A * | 1/1980 | Bartuska et al. | 132/208 |
| 6,290,942 | B1 * | 9/2001 | Nakazato et al. | 424/70.121 |
| 2002/0131947 | A1 * | 9/2002 | Nakanishi | 424/70.12 |
| 2003/0185771 | A1 * | 10/2003 | Kamei et al. | 424/59 |
| 2006/0123564 | A1 * | 6/2006 | Nishizawa et al. | 8/405 |

FOREIGN PATENT DOCUMENTS

| | | | |
|---|---|---|---|
| EP | 1065234 A2 | 1/2001 | |
| EP | 1065234 A2 * | 3/2001 | C08G 77/50 |
| EP | 1213316 A2 | 6/2002 | |
| WO | WO-98/20833 A2 | 5/1998 | |

OTHER PUBLICATIONS

Tetsuo et al., Silicones for powder treatment powders having surface treated with said silicones, and cosmetic materials containing said powders, Jan. 3, 2001, European Patent Application EP 1065234 A2.*

Nomura et al., Deep coloouration hair, Oct. 31, 1984, UK Patent Application GB 2138845 A.*

European Office Action dated Jul. 5, 2012, for European Application No. 03816646.8.

* cited by examiner

*Primary Examiner* — Ali Soroush
(74) *Attorney, Agent, or Firm* — Birch, Stewart, Kolasch & Birch, LLP

(57) ABSTRACT

An organopolysiloxane hair treatment agent (A) represented by the following formula (1),

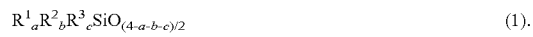

$$R^1_a R^2_b R^3_c SiO_{(4-a-b-c)/2} \qquad (1).$$

The hair treatment agent and cosmetic maintain good conditioning effect for a prolonged period of time.

9 Claims, No Drawings

ORGANOPOLYSILOXANE HAIR TREATMENT AGENT AND HAIR COSMETIC CONTAINING THE TREATMENT AGENT

FIELD OF THE TECHNOLOGY

This invention relates to an organopolysiloxane hair treatment agent and a hair cosmetic comprising the treatment agent. The hair treatment agent increases effects of applying hair rinse, hair conditioner or hair treatment product to the hair, and improves durability of the effects.

BACKGROUND OF THE INVENTION

Nowadays people wash hair everyday and casually perm or color. Hair damages physically or chemically caused by the hair wash, perm or color are serious problems. For damaged hair, conditioning is necessary. As a conditioning agent, oils, cationic surfactants, proteins and hydrolysates thereof, moisturizer, higher alcohols, and emulsions are used. However, conditioning effects of the oils, cationic surfactants, proteins and hydrolysates thereof, moisturizer, higher alcohols, and emulsions are lost by a hair wash and not durable.

To maintain effects of the conditioning, a hair treatment agent has been strongly desired which resists hair wash. As a method to maintain conditioning effects, Japanese Patent Application Laid-Open No. 2001-226236 discloses a method to treat the hair with a methylhydrogenpolysiloxane. The treatment with the polysiloxane is indeed effective but not sufficient. Moreover, unreacted Si—H bonds remain after the treatment, which sometimes cause generation of hydrogen gas. Thus, a hair treatment agent is desired which maintains hair conditioning effect.

Meanwhile, an organopolysiloxane represented by the formula (1)

$$R^1_a R^2_b R^3_c SiO_{(4-a-b-c)/2} \qquad (1)$$

is known from Japanese Patent Application Laid-Open No. 2001-72891.

The invention disclosed in the publication relates to a surface treatment of powder used for cosmetics with the organopolysiloxane. It is described that the surface treated powder is used for a hair cosmetic. However, the publication neither describes nor suggests applying the organopolysiloxane directly on the hair.

DISCLOSURE OF THE INVENTION

The present inventors focused attentions to a specific functionality of the organopolysiloxane of the formula (1) and have found that the aforesaid problem of the conventional conditioning agents can be solved by applying the organopolysiloxane directly on the hair, so that improved and prolonged conditioning effect was attained.

Thus, the present invention provides an organopolysiloxane hair treatment agent (A) represented by the following formula (1), $$R^1_a R^2_b R^3_c SiO_{(4-a-b-c)/2} \qquad (1),\text{ and}$$

a hair cosmetic comprising the hair treatment agent.

The present invention also provides a two-agent hair cosmetic kit composed of a first agent comprising at least one selected from the group consisting of amino-modified silicones, amino acid-modified silicones, and carboxyl-modified silicones, and a second agent comprising the aforesaid hair treatment agent, and a three-agent hair cosmetic kit composed of the aforesaid hair cosmetic kit and an amino-modified silicone.

The aforesaid cosmetic may further comprise at least one selected from an unctuous agent, water, a compound having an alcoholic hydroxyl group, a water-soluble or water-swelling polymer, a surfactant, resins such as a crosslinked organopolysiloxane, and powder and/or coloring agent.

The aforesaid cosmetic is in the form of liquid, milky lotion, cream, solid, paste, gel, multilayer, mousse, spray or stick.

PREFERRED EMBODIMENTS OF THE INVENTION

The present hair treatment agent comprises an organopolysiloxane compound represented by the following formula (1), $$R^1_a R^2_b R^3_c SiO_{(4-a-b-c)/2} \qquad (1).$$

In the formula (1), $R^1$ is an organic group selected from the group consisting of alkyl groups having 1 to 30 carbon atoms, alicyclic groups, aryl groups, aralkyl groups, fluorinated alkyl groups and an organic group represented by following formula (2), $$-C_d H_{2d}-O-(C_2H_4O)_e(C_3H_6O)_f R^4 \qquad (2).$$

In the formula (2), $R^4$ is an alkyl group having 1 to 30 carbon atoms, provided that, when d=e=f=0, the alkyl group has 7 to 30 carbon atoms, or an organic group represented by the formula, $R^5-(CO)-$, wherein $R^5$ is an alkyl group having 1 to 30 carbon atoms, $R^2$ is a group having at least one hydroxyl or alkoxy group having 1 to 6 carbon atoms, which group may be bonded to a silicon atom in the formula (1) via a group having a carbon and/or a silicon atom, $R^3$ is a silicone compound residue represented by the formula (3)

$$-C_x H_{2x}-(SiO)_y-SiR^6_3 \qquad (3)$$

with $R^6$ substituents on the $(SiO)_y$ silicon, wherein $R^6$ is a group selected from the group consisting of alkyl groups having 1 to 30 carbon atoms, alicyclic groups, aryl groups, aralkyl groups, and fluorinated alkyl groups, each of the groups, $R^1$, $R^2$, $R^3$, $R^4$, $R^5$ and $R^6$, if a plurality thereof exist in a molecule, being the same with or different from each other, a, b and c each is a number with $1.0 \leq a \leq 2.5$, $0.001 \leq b \leq 1.5$, and $0.001 \leq c \leq 1.5$, d, e and f each is an integer with $0 \leq d \leq 15$, $0 \leq e \leq 50$, and $0 \leq f \leq 50$, x is an integer with $1 \leq x \leq 5$, and y is an integer with $0 \leq y \leq 500$.

Preferred organopolysiloxane represented by the formula (1) is as follows:

$R^1$ is an alkyl group, a fluorinated alkyl group each having 1 to 6 carbon atoms, or a group represented by the formula, $-C_3H_6$-1-$(C_3H_6O)_f R^4$, wherein $R^4$ is an alkyl group having 7 to 30 carbon atoms and f is an integer with $0 \leq f \leq 50$, $R^2$ is an organic group represented by the following formula (4)

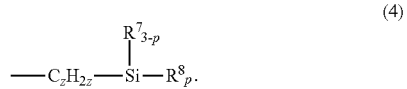

In the formula (4), $R^7$ is a group selected from the group consisting of alkyl groups having 1 to 30 carbon atoms, alicyclic groups, aryl groups, aralkyl groups and fluorinated alkyl groups, $R^8$ is a hydroxyl group or an alkoxy group having 1 to 6 carbon atoms, z is an integer of from 1 to 5, and p is an integer of from 1 to 3.

In the above formula (3) representing $R^3$, $R^6$ is an alkyl group having 1 to 6 carbon atoms, x is 2, and y is an integer of from 1 to 15, and a, b, and c each is a number with $1.2 \leq a \leq 2.3$, $0.05 \leq b \leq 1.0$, and $0.05 \leq c \leq 1.0$.

Examples of $R^1$ include alkyl groups such as methyl, ethyl, propyl, butyl, pentyl, hexyl, heptyl, octyl, nonyl, and decyl groups; alicyclic groups such as cyclopentyl and cyclohexyl groups; aryl groups such as phenyl and tolyl groups; aralkyl groups such as benzyl and phenethyl groups; fluorinated alkyl groups such as trifluoropropyl and heptadecafluorodecyl groups, among which methyl, phenyl and trifluoropropyl groups are preferred.

As $R^1$, an organic group represented by the formula (2) is also preferred, examples of which include residues of higher alcohols such as oleyl alcohol, ally alcohols, cetyl alcohol, and stearyl alcohol, and polyoxyalkylene adducts thereof; residues of higher alcohol alkenyl ethers and polyoxyalkylene adducts thereof; residues of higher fatty acids such as oleic acid, stearic acid and behenic acid, and polyoxyalkylene adducts thereof; and residues of higher fatty acid alkenyl esters and polyoxyalkylene adducts thereof.

The formula (2) is $-O-(C_2H_4O)_e(C_3H_6O)_fR^4$ when d is 0. When e=0 and f=0, the formula is $-O-R^4$ which encompasses residues of higher alcohols such as cetyl alcohol, oleyl alcohol and stearyl alcohol if $R^4$=C7 to C30. When $R^4$ is $R^5-(CO)-$ with $R^5$=C1 to C30, residues of higher fatty acids such as oleic acid and stearic acid are encompassed.

When d is 1 or 2, the formula (2) is $-CH_2-O-(C_2H_4O)_e(C_3H_6O)_fR^4$ or $-C_2H_4-O-(C_2H_4O)_e(C_3H_6O)_fR^4$, respectively. These groups may be bonded to an organopolysiloxane having a Si—OH group by reacting $X(CH_2)_d-O-(C_2H_4O)_e(C_3H_6O)_fR^4$, wherein X is a halogen atom, with the Si—OH of the organopolysiloxane.

When d is 3 or greater, the formula (2) is $-C_dH_{2d}-O-(C_2H_4O)_e(C_3H_6O)_fR^4$, which encompasses residues of the aforesaid higher alcohols, alkenyl ethers or esters of fatty acids. These groups can be bonded to an organopolysiloxane having Si—H group by dehydrogenation reaction of the Si—H group with the higher alcohols or by addition reaction of the Si—H group with the alkenyl ether or esters.

Preferred group represented by the formula (2) include residues of the higher alcohols, higher alcohol alkenyl ethers and polyalkylene oxide adducts thereof.

$R^2$ is an organic group having at least one substituent group selected from a hydroxyl group and alkoxy groups having 1 to 6 carbon atoms such as methoxy, ethoxy, and isopropoxy groups. The substituent group may be bonded to a silicon atom in the organopolysiloxane of the formula (1) directly or via a linkage group having a carbon, or silicon atom such as an alkylene group or an alkylenesilyl group.

Preferred $R^2$ is represented by the following formula.

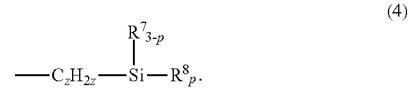

In the formula (4), $R^7$ is a group selected from the group consisting of alkyl groups having 1 to 30 carbon atoms, alicyclic groups, aryl groups, aralkyl groups and fluorinated alkyl groups; $R^8$ is an hydroxyl group or an alkoxy group having 1 to 6 carbon atoms; and z is an integer of from 1 to 5, preferably 2.

In the formula (4), p is an integer of from 1 to 3, preferably 2 or 3, so that the group, $-SiR^7_{3-p}R^8_p$, is a dimethylethoxysilyl group, a diethoxymethylsilyl group or a triethoxysilyl, for example, among which a triethoxysilyl group is more preferred.

These groups may be bonded to an organopolysiloxane chain by an addition reaction of a Si—H group of the organopolysiloxane with vinyltrichlorosilane, vinyltris (β-methoxyethoxy)silane, vinyltrimethoxysilane or vinyltriethoxysilane.

$R^3$ is a silicone compound residue represented by the following formula (3)

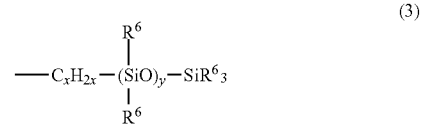

Examples of $R^6$ include alkyl group such as methyl, ethyl, propyl, butyl, pentyl, hexyl, heptyl, octyl, nonyl, and decyl groups; alicyclic groups such as cyclopentyl and cyclohexyl groups; aryl groups such as phenyl and tolyl groups; aralkyl groups such as benzyl and phenetyl groups; and fluorinated alkyl groups such as trifluoropropyl and heptadecafluorodecyl groups, among which methyl, phenyl, and trifluoropropyl groups are preferred.

X is an integer of from 1 to 5, preferably 2, because such group with x being 2 can be formed by a reaction of a vinyl compound and a hydrogensiloxane. Y is an integer of from 0 to 500, preferably 3 to 100. If y is larger than 500, the reactivity with the hydrogensiloxane backbone may be too small.

In the aforesaid formula (1), "a" ranges from 1.0 to 2.5, preferably from 1.2 to 2.3, and b ranges from 0.001 to 1.5, preferably 0.05 to 1.0. If b is smaller than 0.001, interaction with the hair is too small to maintain conditioning effect sufficiently. C ranges from 0.001 to 1.5, preferably from 0.05 to 1.0.

When the organopolysiloxane represented by the formula (1) is used as a hair treatment agent, a weight average molecular weight of the organopolysiloxane preferably ranges from 300 to 100,000, particularly from 1,000 to 10,000. An organopolysiloxane having a weight average molecular weight larger than the aforesaid upper limit may be tacky. An organopolysiloxane having a weight average molecular weight below the aforesaid lower limit may not provide smooth texture characteristic to an organopolysiloxane. In the present invention, a weight average molecular weight is determined by GPC with reference to polystyrenes with a known molecular weight and reduced to the polystyrene.

As described above, the organopolysiloxane represented by the formula (1) can be prepared through an addition reaction and/or dehydrogenation reaction in the presence of platinum catalyst or rhodium catalyst between an organopolysiloxane having a Si—H group and an alkenyl ether, an alkenyl ester of a higher alcohol or a fatty acid or an alkylene oxide addict thereof or a higher alcohol, an alkenyl compound such as vinyltrichlorosilane, vinyltris (β-methoxyethoxy)silane, vinyltrimethoxysilane or vinyltriethoxysilane, and the compound represented by the following formula (5)

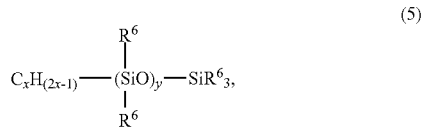

(5)

wherein $R^6$, x and y are as defined above regarding the formula (3).

The organohydrogenpolysiloxane may have a linear structure or a cyclic structure. Preferably, a linear organohydrogenpolysiloxane is used because of higher addition reactivity. Si—H groups may be bonded to a side chain or ends of a silicone backbone. The organohydrogenpolysiloxane is reacted with a mixture of the silicone compound of the formula (5) and other alkenyl compounds in such an amount that a molar ratio of Si—H groups to terminal unsaturated groups ranges from 0.2 to 2.0, preferably from 0.5 to 1.2, to avoid residual unreacted Si—H groups which cause harmful effects such as formation of hydrogen gas.

The aforesaid addition reaction is preferably performed in the presence of platinum catalyst or rhodium catalyst. Examples of suitable catalyst include chloroplatinic acid, alcohol-modified chloroplatinic acid and chloroplatinic acid-vinylsiloxane complex. The amount of catalyst used may be a catalytic amount, but is preferably at most 500 ppm, particularly at most 20 ppm, calculated as platinum or rhodium.

The addition reaction may be carried out in an organic solvent, if needed. Examples of the organic solvent include aliphatic alcohols such as methanol, ethanol, 2-propanol and butanol; aromatic hydrocarbons, such as toluene and xylene; aliphatic or alicyclic hydrocarbons such as n-pentane, n-hexane and cyclohexane; and halogenated hydrocarbons such as dichloromethane, chloroform and carbon tetrachloride.

Any reaction conditions of the addition reaction may be employed. Preferably, the reaction is performed under reflux of the solvent for 1 to 10 hours.

In the present invention, the organopolysiloxane hair treatment agent (A) can be used in various ways. It can be used alone in the form of a dispersion or a solution in an organic solvent which is applied directly on the hair; it can be used in a two-agent kit composed of an aqueous or non-aqueous first agent selected from the group consisting of amino-modified silicone, amino acid-modified silicone and carboxyl-modified silicone, and the present hair treatment agent (A) as a second agent; and it can be used in a three-agent kit composed of a first agent comprising an aqueous or non-aqueous amino-modified silicone, a second agent comprising the present hair treatment agent (A), and a third agent comprising an aqueous or non-aqueous amino-modified silicone.

Preferably, an amino-modified silicone is used as the first agent and the present hair treatment agent is used as the non-aqueous second agent. Alternatively, an amino-modified silicone is used as the first agent, the present hair treatment agent is used as the non-aqueous second agent, and an aqueous or non-aqueous amino-modified silicone is used as the third agent. In both the two-agent and the three-agent kits, it was found that conditioning effect is maintained well by a synergistic effect of the amino-modified silicone and the present hair treatment agent.

Examples of the amino-modified silicone include those having amino groups grafted to a silicone backbone, those having an amino group bonded to either one end of a silicone backbone, those having amino groups bonded to both ends of a silicone backbone, those having amino groups at both ends of a silicone backbone and an amino group grafted to the silicone backbone, and those having a silicone side chain and an amino group both grafted to a silicone backbone. Preferably, the amino-modified silicone represented by the following formula is used.

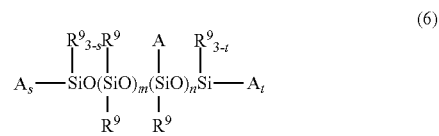

(6)

In the formula (6), A is —$R^{10}NH_2$ or —$R^{10}NHR^{11}NH_2$, wherein $R^{10}$ and $R^{11}$ are alkylene groups having 1 to 8 carbon atoms, $R^9$ may be the same with or different from each other and is selected from the group consisting of alkyl groups having 1 to 30 carbon atoms, alicyclic groups, aryl groups, aralkyl groups, and fluorinated alkyl groups, m and n may be the same with and different from each other and are integers of from 0 to 300, and s and t may be the same with or different from each other and are integers of from 0 to 3 with 1≤n+s+t.

Examples of $R^9$ include alkyl group such as methyl, ethyl, propyl, butyl, pentyl, hexyl, heptyl, octyl, nonyl, and decyl groups; alicyclic groups such as cyclopentyl and cyclohexyl groups; aryl groups such as phenyl and tolyl groups; aralkyl groups such as benzyl and phenetyl groups; and fluorinated alkyl groups such as trifluoropropyl and heptadecafluorodecyl groups, among which methyl, phenyl, and trifluoropropyl groups are preferred.

Examples of $R^{10}$ and $R^{11}$ include methylene, ethylene, propylene, butylene, and pentylene groups, among which methylene, ethylene and propylene groups are preferred.

The present hair cosmetic may further comprise various components incorporated in conventional cosmetics. Those components may be incorporated not only in one agent system composed of the component (A), but also in two- or three-agent kit as a whole, that is, the components may be incorporated in one or more of the agents from first to third one. These components will be explained below.

The present cosmetic may comprise one or more of unctuous agent (B). Any conventional unctuous agents can be used whether they are in the form of solid, semisolid or liquid. Examples of the unctuous agents include natural animal or plant oils, semi-synthetic oils, hydrocarbon oils, higher alcohol oils, ester oils and conventional silicone oils.

Examples of the natural animal or plant oils and semi-synthetic oils include avocado oil, linseed oil, almond oil, Chinese wax, perilla oil, olive oil, cacao butter, kapok wax, kaya oil, carnauba wax, liver oil, candellila wax, beef tallow, beef foot oil, beef bone fat, hydrogenated beef tallow, apricot kernel oil, spermaceti, hydrogenated oil, wheat germ oil, sesame oil, rice germ oil, rice branoil, sugarcane wax, sasanquaoil, safflower oil, shea butter, Chinese tung oil, cinnamon oil, jojoba wax, shellac wax, turtle oil, soybean oil, tea seed oil, tsubaki oil, evening primrose oil, corn oil, lard, rape seed oil, Japanese tung oil, rice-bran wax, germ oil, horse fat, persic oil, palm oil, palm kernel oil, castor oil, hydrogenated castor oil, caster oil fatty acid methyl ester, sunflower oil, grape seed oil, bayberry wax, jojoba oil, macadamia nut oil, bees wax, mink oil, cottonseed oil, cotton wax, Japan wax, haze kernel oil, montan wax, coconut oil, hydrogenated coconut oil, tricoconut oil fatty acid glyceride, mutton-tallow, peanut oil, lanolin, liquid lanolin, reduced lanolin, lanolin alcohol, hard lanolin, lanolin acetate, lanolin fatty acid isopropyl, hexyl laurate, POE lanolin alcohol ether, POE lanolin alcohol acetate, lanolin fatty acid polyethylene glycol, POE hydrogenated lanolin alcohol ether, and egg yolk oil, wherein the term "POE" stands for polyoxyethylene.

Examples of the hydrocarbon oil include ozokerite, squalane, squalene, ceresine, paraffin, paraffin wax, liquid paraffin, pristane, polyisobutylene, microcrystalline wax and Vaseline; and those of a higher fatty acid which can be mixed include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid and 12-hydroxystearic acid.

Examples of the higher alcohol oils include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, POE cholesterol ether, monostearyl glycerin ether (batyl alcohol) and monooleyl glyceryl ether (cerakyl alcohol).

Examples of the ester oil include diisobutyl adipate, 2-hexyldecyl adipate, di-2-heptylundecyl adipate, N-alkylglycol monoisostearate, isocetyl isostearate, trimethylolpropane triisostearic acid ester, ethylene glycol di-2-ethylhexanoic acid ester, cetyl 2-ethylhexanoate, trimethylolpropane tri-2-ethylhexanoic acid ester, pentaerythritol tetra-2-ethylhexanoic acid ester, cetyl octanoate, octyldodecyl gum ester, oleyl oleate, octyldodecyl oleate, decyl oleate, neopentyl glycol dicapric acid ester, triethyl citrate, 2-ethylhexyl cinnamate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethylocanoate, ethyl laurate, hexyl laurate, N-lauroyl-L-glutaminic acid 2-octyldodecyl ester and diisostearyl malic acid; and examples of glyceride oil which can be mixed therein include acetoglyceride, triisooctanoic acid glycride, triisostearic acid glyceride, triisopalmitic acid glyceride, tri-2-ethylhexanoic acid glyceride, monostearic acid glyceride, di-2-heptylundecanoic acid glyceride, trimyristic acid glyceride and myristic acid isostearic acid diglyceride.

Examples of the conventional silicone oil include organopolysiloxanes having a viscosity of from a low value to a high value, preferably from 0.65 to 1,000,000 mm$^2$/s, such as dimethylpolysiloxane, methylphenylpolysiloxane, methylhydrogenpolysiloxane and a copolymer of dimethylsiloxane and methylphenylsiloxane; cyclic siloxanes, such as octamethylcyclotetrasiloxane, decamethylcyclopentasiloxane, dodecamethylcyclohexasiloxane, tetramethyl-tetrahydrogencyclotetrasiloxane; silicone rubbers, such as gummy dimethylpolysiloxanes having high polymerization degrees and gummy dimethylsiloxane-methylphenylsiloxane copolymers having high polymerization degrees; and cyclosiloxane solutions of silicone rubber, trimethylsiloxysilicate, cyclosiloxane solutions of trimethylsiloxysilicate, higher alkoxy-modified silicones such as stearoxysilicone, higher fatty acid-modified silicones, alkyl-modified silicones, siliconols, fluorine-modified silicones, and solutions of silicone resins in a cyclic siloxane.

Examples of fluorine-containing oil include perfluoropolyether, perfluorodecalin and perfluorooctane.

A content of these unctuous agents may vary depending on the form of the cosmetic and range from 0.01 to 99 wt % based on a total weight of the cosmetic.

The present hair cosmetic may further comprise (C) water according to a purpose of the cosmetic. A content of water (C) may vary depending on the form of the cosmetic and ranges from 0.01 to 99 wt % based on a total weight of the cosmetic.

The present cosmetic may further comprise one or more of a compound (D) having at least one alcoholic hydroxyl group per molecule, depending on a purposes of the cosmetic. Examples of the compoud (D) include lower alcohols, such as ethanol and isopropanol; sugar alcohols, such as sorbitol and maltose; sterols, such as cholesterol, sitosterol, phytosterol and lanosterol; and polyhydric alcohols such as butylene glycols, propylene glycols, dibutylene glycols, and pentylene glycols. The compound (D) may be incorporated in the cosmetic in an amount of from 0.1 to 98 wt % based on a total weight of the cosmetic.

The present cosmetic may further comprise one or more of a water-soluble or water-swelling polymer (E). Examples of the water-soluble or water-swelling polymer include plant origin polymers, such as gum arabic, tragacanth, galactan, carob gum, guar gum, karaya gum, carrageenan, pectin, agar, quince seed, starch (rice, corn, potato, wheat), algae colloid, tranto gum and locust bean gum; microbial polymers, such as xanthan gum, dextran, succinoglucan and pullulan; animal polymers, such as collagen, casein, albumin and gelatin; starch polymers, such as carboxymethyl starch and methylhydroxypropyl starch; cellulose polymers, such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethylcellulose, crystalline cellulose and powdery cellulose; alginic acid polymers, such as sodium alginate and propylene glycol ester of alginic acid; vinyl polymers, such as polyvinyl methyl ether and carboxyvinyl polymer; polyoxyethylene polymers; polyoxyethylene-polyoxypropylene copolymers; acrylic polymers, such as sodium polyacrylate, polyethylacrylate and polyacrylamide; other synthetic water-soluble polymers, such as polyethyleneimines and cationic polymers; and inorganic water-soluble polymers, such as bentonite, aluminum magnesium silicate, montmorillonite, beidellite, nontronite, saponite, hectorite and silicic acid anhydride. The water-soluble polymer encompasses film-forming agents, such as polyvinyl alcohol and polyvinyl pyrrolidine, are also included. It may be incorporated in the cosmetic in an amount of from 0.1 to 25 wt % based on a total weight of the cosmetic.

The present hair cosmetic may further comprise one or more of a surfactant (F) according to a purpose of the cosmetic. Examples of the surfactant include anionic, cationic, nonionic and amphoteric surfactants and are not limited to a particular one. Any surfactant can be used so long as it is used in ordinary cosmetics.

Examples of the anionic surfactant include fatty acid soap, such as sodium stearate or triethanolamine palmitate; alkyl ether carboxylic acids and salts thereof; salts of amino acid-fatty acid condensates; alkanesulfonates; alkenesulfonates; sulfonated fatty acid esters; sulfonated fatty acid amides;

sulfonates of formaldehyde condensate type; alkylsulfates; higher secondary alcohol sulfates; alkyl and aryl ether sulfates; fatty acid ether sulfates, fatty acid alkylolamide sulfates; ether sulfates, such as Turkeky red oil; alkyl phosphates; ether phosphates; alkyl aryl ether phosphates; amide phosphates; and active agents of N-acylamino acid type.

Examples of the cationic surfactant include amine salts, such as alkylamie salts, polyamines and aminoalcohol fatty acid derivatives, quaternary alkylammonium salts, quaternary arylammonium salts, pyridinium salts and imidazolium salts.

Examples of the nonionic surfactant include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ehter, polyoxyethylene phytosterol ether, polyoxyethylene cholestanol ether, polyoxyethylene cholesteryl ether, linear or branched polyoxyalkylene-modified organopolysiloxanes, linear or branched organopolysiloxanes modified with both polyoxyalkylene and alkyl groups, linear or branched polyglycerin-modified organopolysiloxanes, alkanolamides, sugar ethers and sugar amides; and examples of a usable amphoteric surfactant include betaine, aminocarboxylates and imdazoline derivatives. The surfactant may be incorporated in the cosmetic preferably in an amount of from 0.1 to 20 wt %, particularly 0.2 to 10 wt %, based on a total weight of the cosmetic.

The present cosmetic may further comprise one or more of a crosslinked organopolysiloxane (G), depending on a purpose of the cosmetic. The crosslinked organopolysiloxane preferably has been swelled with a silicone having a low viscosity of from 0.65 to 10.0 mm$^2$/sec (25° C.) in an amount larger than a weight of the organopolysiloxane (G). Preferred crosslinked organopolysiloxane is a reaction product of an organopolysiloxane having at least two alkenyl groups per molecule and an organohydrogenpolysiloxane having a Si—H bond. The crosslinked organopolysiloxane may have at least one moiety selected from polyoxyalkylene, polygrycerol, alkyl, alkenyl, aryl and fluoroalkyl moieties. The crosslinked organopolysiloxanes may be incorporated in the cosmetic preferably in an amount of from 0.1 to 50 wt %, more preferably from 1 to 30 wt %, based on a total weight of the cosmetic.

The present cosmetic may further comprise one or more of a conventional silicone resin (H). Preferred silicone resin is an acrylsilicone resin such as an acryl silicone graft copolymer and acryl silicone block copolymer. Use may be made of an acrylsilicone resin having at least one moiety selected from the group consisting of pyrrolidone moieties, long-chain alkyl moieties, polyoxyalkylene moieties, fluoroalkyl moieties and anionic moieties, for example, carboxylic acid moieties.

Preferably, this silicone resin is a silicone compound having a network structure represented as MQ, MDQ, MT, MDT, or MDTQ. Use may be made of a silicone network compound having at least one moiety selected from the group consisting of pyrrolidone, long-chain alkyl, polyoxyalkylene, fluoroalkyl, and amino moieties.

The acryl silicone resins or silicone network compounds may be incorporated in the cosmetic preferably in an amount of from 0.1 to 20 wt %, more preferably from 1 to 10 wt %.

The present cosmetic may further comprise one or more of powder and/or coloring agent (I) depending on a purpose of the cosmetic. Any powder conventionally used in cosmetics can be used irrespective of its form, for example, spherical, acicular or tabular; its size, for example, fume state, fine grain or pigment grade; and its structure, for example, porous or nonporous. Examples include inorganic powder, organic powder, metal salt surfactant powder, colored pigments, pearl pigments, metallic powder pigments and natural pigments.

Examples of the inorganic powder include titanium dioxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, ruby mica, biotite, lipidolite, silicic acid, silicic acid anhydride, aluminum silicate, magnesium silicate, aluminum magnesium silicate, calcium silicate, barium silicate, strontium silicate, metal salts of tungstic acid, hydroxyapatite, vermiculite, haidilite, bentonite, montmorillonite, hectorite, zeolite, ceramics powder, calcium secondary phosphate, alumina, aluminum hydroxie, boron nitride and silica.

Examples of the organic powder include polyamide powder, polyester powder, polyethylene powder, polypropylene powder, polystyrene powder, polyurethane powder, benzoguanamine powder, polymethylbenzoguanamine powder, polytetrafluoroethylene powder, polymethylmethacrylate powder, cellulose powder, silk powder, nylon powder such as 12-nylon powder or 6-nylon powder, crosslinked dimethylsilicone fine powder, polymethylsilsesquioxane fine powder, powder of crosslinked silicone composite with polymethylsilsesquioxane bonded to the silicone, styrene-acrylic acid copolymer powder, divinylbenzene-styrene copolymer powder, vinyl resin powder, urea resin powder, phenol resin powder, fluororesin powder, silicone resin powder, acrylic resin powder, melamine resin powder, epoxy resin powder, polycarbonate resin powder, microcrystalline fiber powder, starch powder and lauroyl lysine powder.

Examples of the metal salt surfactant powder (metal soap powder) include powders of zinc stearate, aluminum stearate, calcium stearate, magnesium stearate, zinc myristate, magensium myristate, zinc cetylphosphate, calcium cetylphosphate and zinc sodium cetylphosphate.

Examples of the colored pigment include red pigments, such as iron oxide, iron hydroxide and iron titanate; inorganic brown pigments, such as γ-iron oxide; inorganic yellow pigments, such as iron oxide yellow and loess; inorganic black pigments, such as iron oxide black and carbon black; inorganic violet pigments, such as manganese violet and cobalt violet; inorganic green pigments, such as chromium hydroxide, chromium oxide, cobalt oxide and cobalt titanate; inorganic blue pigments, such as Prussian blue and ultramarine blue; lakes of tar pigments; lakes of natural dyes; and a composite powder of two or more of above.

Examples of the pearl pigment include titanium oxide-coated mica, bismuth oxychloride, titanium oxide-coated bismuth oxychloride, titanium oxide-coated talc, fish scales, and titanium oxide-coated colored mica. Examples of the metallic powder pigment include aluminum powder, copper powder and stainless powder. Examples of the tar pigment include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207; and examples of the natural pigment include powders of carminic acid, laccaic acid, carthamin, bradilin and crocin.

The powder may be used as in a composite form in an amount not to adversely affect the effects of the present invention or may be treated with a commonly used oil, silicone oil, fluoro compound, or surfactant. The powder may be used as a mixture of two or more thereof, if desired. The powder is incorporated in the cosmetic preferably in an amount of from 0.1 to 99 wt % based on a total weight of the cosmetic.

To the present cosmetic may further comprise ingredients used in general cosmetics such as oil-soluble gelling agents, clay minerals modified with organic compounds, resins, ultraviolet absorbents or scattering material, moisturizing agents, antiseptics, antimicrobial agents, perfume, salts, antioxidants, pH regulators, chelating agents, refrigerant, anti-inflammatory agents, skin beautifying components (a skin whitener, a cell activator, a rough dry skin improver, a blood circulation promoter, a skin astringent and an anti-seborrheic agent), vitamins, amino acids, nucleic acids, hormones and clathrate compounds, and polymers for hair setting, in an amount not to have adverse influences on the effects of the present invention.

Examples of the oil-soluble gelling agent include metal soaps, such as aluminum stearate, magnesium stearate and zinc myristate; amino acid derivatives, such as N-lauroyl-L-glutamic acid and $\alpha,\gamma$-di-n-butylamine; dextrin fatty acid esters, such as dextrinpalmitic acid ester, dextrin stearic acid ester and dextrin 2-ethylhexaminic acid palmitic acid ester; sucrose fatty acid esters, such as sucrose palmitic acid ester and sucrose stearic acid ester; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay.

Examples of the ultraviolet absorbent include ultraviolet absorbents of benzoic acid type, such as p-aminobenzoic acid; those of anthranilic acid type, such as methyl anthranilate; those of salicylic acid type, such as methyl salicylate; those of succinic acid type, such as octyl p-methoxysuccinate; those of benzophenone type, such as 2,4-dihydroxybenzophenone; those of urocanic acid type, such as ethyl urocanate; and those of dibenzoylmethane type, such as 4-t-butyl-4'-methoxydibenzoylmethane. Examples of ultraviolet scattering material include titanium oxide fine powder, fine powder of titanium oxide containing iron, zinc oxide fine powder, cerium oxide fine powder, a composed powder of two or more of these and powder which absorbs and scatters ultraviolet.

Examples of the moisturizing agent include glycerin, sorbitol, propylene glycol, dipropylene glycol, 1,3-butylene glycol, glucose, xylitol, maltitol, polyethylene glycol, hyaluromic acid, chondroitin sulfuric acid, pyrrolidone carboxylic acid, polyoxyethylene glycoside, and polyoxypropylene methylglycoside.

Examples of the antiseptic agent include alkyl p-hydroxybenzoates, benzoic acid, sodium benzoate, sorbic acid, potassium sorbate and phenoxyethanol; and those of an antimicrobial agent which can be added include benzoic acid, salicylic acid, carbolic acid, sorbic acid, alkyl p-hydroxybenzoates, p-chlorometacresol, hexachlorophene, benzalkonium chloride, chlorhexidine chloride, trichlorocarbanilide, photosensitizer and phenoxyethanol.

Examples of the antioxidant include tocopherol, butylhydroxyanisole, dibutylhydroxytoluene and phytic acid; those of a pH regulator which can be added include lactic acid, citric acid, glycolic acid, succinic acid, tartaric acid, dl-malic acid, potassium carbonate, sodium hydrogen carbonate and ammonium hydrogen carbonate; those of a chelating agent which can be added include alanine, sodium ethylenediaminetetraacetate, sodium polyphosphate, sodium metaphosphate and phosphoric acid; those of a refrigerant which can be added include L-menthol and camphor; and those of an anti-inflammatory agent which can added include allantoin, glycyrrhizin and salts thereof, glycyrrhetinic acid and stearyl glycyrrhetinate, tranexamic acid and azulene.

Examples of the skin-beautifying component include whitening agents, such as placenta extract, arbutin, glutathione and Yukinoshita extract; cell activators, such as royal jelly, photosensitizer, cholesterol derivatives and calf blood extract; rough dry skin improvers; blood circulation improvers, such as nonylic acid vanillyl amide, benzyl nicotinate, $\beta$-butoxyethyl nicotinate, capsaicin, zingerone, cantharis tincture, ichtammol, caffeine, tannic acid, $\alpha$-borneol, tocopheryl nicotinate, inositol hexanicotinate, cyclandelate, cinnarizine, tolazoline, acetyl choline, verapamil, cepharanthin and $\gamma$-oryzanol; skin astringents, such as zinc oxide and tannic acid; and anti-seborrheic agents, such as sulfur and thianthol.

Examples of the vitamin include vitamin A, such as vitamin A oil, retinol, retinyl acetate and retinyl palmitate; vitamin B, including vitamin B2 such as riboflavin, riboflavin butyrate and flavin adenine nucleotide, vitamin B6 such as pyridoxine hydrochloride, pyridoxine dioctanoate and pyridoxine tripalmitate, vitamin B12 and its derivatives, and vitamin B15 and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitamin E, such as $\alpha$-tocopherol, $\beta$-tocopherol, $\gamma$-tocopherol, dl-$\alpha$-tocopheryl acetate, dl-$\alpha$-tocopheryl nicotinate and dl-$\alpha$-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of the amino acid include glycine, valine, leucine, isoleucine, serine, threonine, phenylaranine, alginine, lysine, aspartic acid, aspartic acid, glutamic acid, cystine, cysteine, methionine, and tryptophan; those of a nucleic acid which can be added include deoxyribonucleic acid; and those of hormone which can be added include estradiol and ethenyl estradiol.

Examples of the polymer for hair setting include amphoteric, anionic, cationic, and nonionic polymers, such as polymers of polyvinyl pyrrolidone type such as polyvinyl pyrrolidone, vinyl pyrrolidone/vinyl acetate copolymers; acidic polymers of vinyl acetate ether type such as methyl vinyl ether/maleic acid anhydride alkyl half ester copolymer; polymers of acidic poly vinyl acetate type such as vinyl acetate/crotonic acid copolymer; acidic acrylic polymers such as (meth)acrylic acid/alkyl (meth) acrylate copolymer, (meth) acrylic acid/alkyl (meth) acrylate/alkyl acrylic amide copolymer, and amphoteric acrylic polymer such as N-methacryloylethyl-N,N-dimethylammonium alpha-N-methylcarboxybetaine/alkylmetahcrylate copolymer, hydroxypropyl (metha)acrylate/butylaminoethyl methacrylate/octyl amide of acrylic acid copolymer. Use is also made of naturally occurring polymers such as cellulose or derivatives thereof, keratin, collagen and derivatives thereof.

The present hair cosmetic may be in the form of liquid, milky lotion, cream, solid, paste, gel, multilayer, mousse, spray or stick.

EXAMPLES

The present invention will be explained in detail with reference to Examples, but not limited thereto. In the following, "%" means % by weight unless otherwise specified.

Synthesis Example 1

In a reaction vessel, 600 parts by weight of organohydrogensiloxane represented by the following average structural formula (7) and 800 parts by weight of toluene were placed, to which 2 parts by weight of a 0.5% solution of chloroplatinic acid in toluene was added.

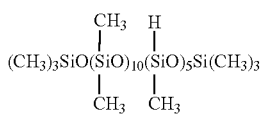
(7)

Then, 1,382 parts by weight of an organopolysiloxane represented by the following structural formula (8) was added dropwise.

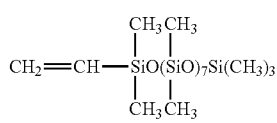
(8)

The reaction was performed for 6 hours under reflux of the solvent while adding dropwise 110 parts by weight of vinyltriethoxysilane to the reaction vessel.

The reaction mixture was heated under a reduced pressure to distill off the solvent. Thus, the organopolysiloxane hair treatment agent represented by the following average structural formula (9) was obtained.

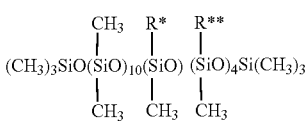
(9)

wherein,

R'=—$C_2H_4Si(OEt)_3$ and

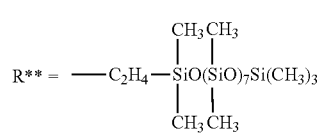

The product obtained was colorless transparent liquid having a viscosity of 57 mm$^2$/s (at 25° C.), a specific gravity of 0.958 (at 25° C.) and a weight average molecular weight (Mw) of 4400 (reduced to polystyrene) determined by GPC.

Synthesis Example 2

In a reaction vessel, 416 parts by weight of organohydrogensiloxane represented by the following average structural formula (10) and 400 parts by weight of toluene were placed, to which 2 parts by weight of a 0.5% solution of chloroplatinic acid in toluene was added.

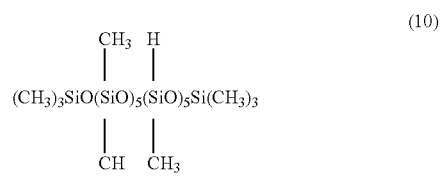
(10)

Then, a mixture or 676 parts by weight of the organopolysiloxane represented by the above formula (7) with 168 parts by weight of 1-dodecene was added dropwise to the reaction vessel. The reaction was performed for 6 hours under reflux of the solvent while adding 100 parts by weight of vinyltriethoxysilane into the reaction vessel. Then, the reaction mixture was heated under a reduced pressure to distill off the solvent. Thus, organopolysiloxane hair treatment agent represented by the following average structural formula (11) was obtained.

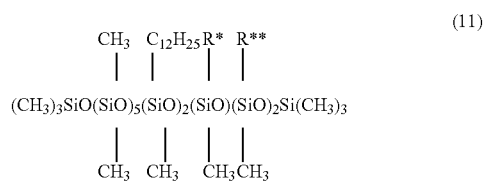
(11)

wherein, R* and R** are as defined above in Synthesis Example 1.

The product obtained was colorless transparent liquid having a viscosity of 48 mm$^2$/s (at 25° C.), a specific gravity of 0.951 (at 25° C.) and a weight average molecular weight (Mw) of 2900 (reduced to polystyrene) determined by GPC.

Synthesis Example 3

In a reaction vessel, 608 parts by weight of the organohydrogenpolysiloxane represented by the following average structural formula (12) and 360 parts by weight of toluene were mixed, to which 0.2 parts by weight of a 2% solution of chloroplatinic acid in toluene was added.

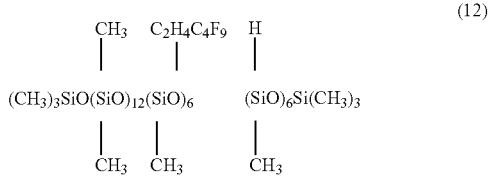
(12)

Then, 740 parts by weight of the organopolysiloxane represented by the aforesaid formula (8) was added dropwise under reflux and subjected to a reaction. The reaction was performed for 6 hours under reflux of the solvent while adding dropwise 45 parts by weight of vinyltriethoxysilane to the reaction vessel. The reaction mixture was heated under a reduced pressure to distill off the solvent. Thus, the organopolysiloxane hair treatment agent represented by the following average structural formula (13) was obtained.

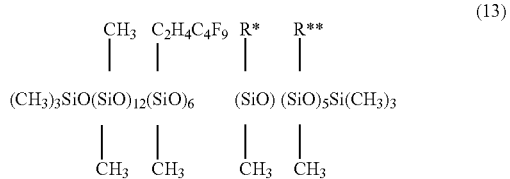

(13)

wherein R* and R** are as defined above Synthesis Example 1.

The product obtained was colorless transparent liquid having a viscosity of 63 mm²/s (at 25° C.), a specific gravity of 1.053 (at 25° C.) and a weight average molecular weight (Mw) of 7000 (reduced to polystyrene) determined by GPC.

Synthesis Example 4

In a reaction vessel, 600 parts by weight of organohydrogensiloxane represented by the aforesaid average structural formula (7) and 400 parts by weight of toluene were placed, to which 2 parts by weight of a 0.5% solution of chloroplatinic acid in toluene was added. Then, 1100 parts by weight of the organopolysiloxane represented by the aforesaid formula (8) was added and subjected to a reaction.

Subsequently, 280 parts by weight of polypropyleneglycol oleyl allyl ether, available under the trade name of RG-1252 from Nippon Nyukazai Co., Ltd. was added. Then, 110 parts by weight of vinyltriethoxysilane was added dropwise and subjected to a reaction under reflux of the solvent for 3 hours. The reaction product was heated at a reduced pressure to distill off the solvent. Thus, the organopolysiloxane hair treatment agent represented by the following average structural formula (14) was obtained.

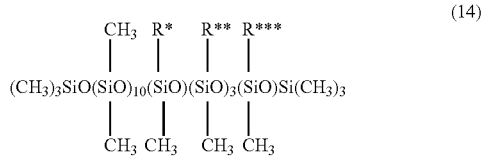

(14)

wherein R* and R are as defined in Synthesis Example 1 and R is —$C_3H_6O(C_3H_6O)_3C_{18}H_{35}$.

The product obtained was colorless transparent liquid having a viscosity of 61 mm²/s (at 25° C.), a specific gravity of 0.955 (at 25° C.) and a weight average molecular weight (Mw) of 4080 (reduced to polystyrene) determined by GPC.

Example 1

Hair Spray (One-Agent Type)

| Components | wt % |
|---|---|
| 1. Synthesis Example 2 | 5.0 |
| 2. Ethanol | 95.0 |

The components described above were mixed. The mixture was packed in a spray container to prepare a hair spray. The hair spray obtained was tested by five female panelists and rated according to the following criteria by comparing the hair to which the hair spray was applied with the reference hair which was not applied with the hair spray in terms of easiness to comb, moisturizing feel, softness, and gloss.

| Mark | Easiness to comb | Moisturized feel, softness, and gloss |
|---|---|---|
| 5 | Much easier | Significant |
| 4 | A little easier | A little more than the reference level |
| 3 | Reference level | Reference level |
| 2 | A little difficult than the reference | A little less than the reference level |
| 1 | Much difficult | None |

The points were averaged and used for evaluation as shown below.

Evaluation according to an averaged mark:

| Averaged mark | |
|---|---|
| 4.5 or higher | A |
| 3.5 to below 4.5 | B |
| 2.5 to below 3.5 | C |
| 1.5 to below 2.5 | D |
| below 1.5 | E |

Comparative Example 1

A hair spray was prepared as in Example 1 except that a methylhydrogenpolysiloxane was used in place of the organopolysiloxane prepared in Synthetic Example 2.

Results of Example 1 and Comparative Example 1 are as shown in Table 1 below.

TABLE 1

| | Example 1 | Comparative Example 1 |
|---|---|---|
| Easiness to comb | A | A |
| Moisturized feed | A | B |
| Softness | A | A |
| Gloss | A | B |

As is evident from Table 1, the hair treated with the hair spray of the present invention was easy to comb, moisturized, soft and glossy compared with the hair treated with methylhydrogenpolysiloxane.

Examples 2-5, Comparative Examples 2-4

Hair treatment agents each having the formulation shown in Table 2 were prepared.

TABLE 2

|  |  | Ex*3. 2 | Ex. 3 | Ex. 4 | Ex. 5 | Comp. Ex.*4 2 | Comp. Ex. 3 | Comp. Ex. 4 |
|---|---|---|---|---|---|---|---|---|
|  | First agent |  |  |  |  |  |  |  |
| 1 | Amino-modified silicone*1 | 5 | 5 | 5 | — | 5 | 5 | 5 |
| 2 | Cetanol | 8 | 8 | 8 | — | 8 | 8 | 8 |
| 3 | Stearyl trimethyl ammonium chloride | 3.5 | 3.5 | 3.5 | — | 3.5 | 3.5 | 3.5 |
| 4 | Glycerin | 5 | 5 | 5 | — | 5 | 5 | 5 |
| 5 | Purified water | 78.5 | 78.5 | 78.5 | — | 78.5 | 78.5 | 78.5 |
|  | Second agent |  |  |  |  |  |  |  |
| 1 | Synthesis example 1 | 6 | — | — | 6 | — | — | — |
| 2 | Synthesis example 3 | — | 6 | — | — | — | — | — |
| 3 | Synthesis example 4 | — | — | 6 | — | — | — | — |
| 4 | Methylhydrogen polysiloxane | — | — | — | — | 6 | 6 | — |
| 5 | Ethanol | 94 | 94 | 94 | 94 | 94 | 94 | 100 |
|  | Third agent |  |  |  |  |  |  |  |
| 1 | Amino-modified silicone*1 | — | — | 2 | — | — | 2 | — |
| 2 | Highly polymerized methylpolysiloxane solution*2 | — | — | 5 | — | — | 5 | — |
| 3 | Cetanol | — | — | 8 | — | — | 8 | — |
| 4 | Stearyl trimethyl ammonium chloride | — | — | 3.5 | — | — | 3.5 | — |
| 5 | Glycerin | — | — | 3 | — | — | 3 | — |
| 6 | Purified water | — | — | 78.5 | — | — | 78.5 | 100 |

*1 Amino-modified silicone: KF-8005, ex Shin-Etsu Chemical Co., Ltd.
*2 Solution of a Highly polymerized methylpolysiloxane: KF-9013, ex Shin-Etsu Chemical Co., Ltd.
*3 "Ex." stands for Example.
*4 "Comp. Ex." stands for Comparative Example.

Each hair treatment agent was evaluated using hair bundles for testing.

The hair bundle for testing was a bundle of ordinary hair with a length of 20 cm and a total weight of 6.0 g which had been shampooed and breached with a breaching agent.

In Examples 2 and 3, the hair bundle was coated with one gram of a first agent followed by washing with water, and then coated with one gram of a second agent followed by drying; in Example 4, the hair bundle was treated with a first agent and then a second agent as described above, and then coated with one gram of a third agent; and in Example 5, the hair bundle was washed and then coated with one gram of a second agent. Each of thus treated hair bundle was processed under the conventional conditions by treating with a conventional hair treatment product, rinsing and drying.

Subsequently, the process consisting of shampooing, hair treatment with a treatment product and drying was repeated 20 times consecutively.

The hair bundles immediately after treated with the present hair treatment agent and those after 20 cycles of the processing were compared with as ordinary hair being a reference in easiness to comb, moisturized feel, softness, and gloss. Results are as shown in the following Table.

TABLE 3

|  | Example 2 | Example 3 | Example 4 | Example 5 | Comp. Ex. 2 | Comp. Ex. 3 | Comp. Ex. 4 |
|---|---|---|---|---|---|---|---|
| Immediately after treatment |  |  |  |  |  |  |  |
| Easiness to comb | A | A | A | A | B | A | B |
| Moisturized feel | A | A | A | A | B | B | B |
| Softeness | A | A | A | A | A | A | B |
| Gloss | A | A | A | A | B | A | B |

TABLE 3-continued

|  | Example 2 | Example 3 | Example 4 | Example 5 | Comp. Ex. 2 | Comp. Ex. 3 | Comp. Ex. 4 |
| --- | --- | --- | --- | --- | --- | --- | --- |
| After 20-cycle processing |  |  |  |  |  |  |  |
| Easiness to comb | A | A | A | B | D | C | D |
| Moisturized feel | A | A | A | A | D | B | D |
| Softeness | A | A | A | A | D | B | D |
| Gloss | A | A | A | B | D | C | D |

As shown in Table 3, compared with the hair cosmetic of Comparative Examples, the hair treatment cosmetics of the present invention were superior in all the aspects, i.e., easiness to comb, moisturizing effect, softening effect and gloss, indicating improvement in durability of hair treatment applied to the hair.

In Examples 2 to 4, the hair after 20-cycle processing showed the same result as that of the hair immediately after treated, indicating excellent resistance to shampooing. Especially, Examples 2 and 5, wherein the present treatment agent is used together with the amino-modified silicone, durable coating film on the hair was formed to maintain smoothness in combing and gloss, compared with Comparative Example 4. Although, the effect was demonstrated by using amino-modified silicones, the same effect is attained with amino acid-modified silicones and carboxyl-modified silicones hair treatment agent.

The invention claimed is:

1. A method of conditioning hair, said method comprising a step of applying an organopolysiloxane hair treatment composition to said hair;

wherein said organopolysiloxane hair treatment composition comprises:

an organopolysiloxane represented by the following formula (1), dispersed or dissolved in an organic solvent,

wherein $R^1$ is an organic group selected from the group consisting of alkyl groups having 1 to 30 carbon atoms, alicyclic groups, aryl groups, aralkyl groups, fluorinated alkyl groups and an organic group represented by following formula (2),

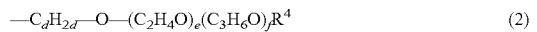

wherein $R^4$ is an alkyl group having 1 to 30 carbon atoms, provided that, when d=e=f=0, said alkyl group has 7 to 30 carbon atoms, or an organic group represented by the formula, $R^5$—(CO)—, wherein $R^5$ is an alkyl group having 1 to 30 carbon atoms, $R^2$ is a group having at least one hydroxyl group or alkoxy group having 1 to 6 carbon atoms, wherein said hydroxyl group or alkoxy group is bonded to a silicon atom in the formula (1) directly or via an alkylenesilyl group, $R^3$ is a silicone compound residue represented by the following formula (3),

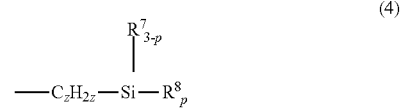

wherein $R^6$ is a group selected from the group consisting of alkyl groups having 1 to 30 carbon atoms, alicyclic groups, aryl groups, aralkyl groups, and fluorinated alkyl groups, wherein when two or more of the groups $R^1$, $R^2$, $R^3$, $R^4$, $R^5$ or $R^6$, respectively, are present in a molecule, such are the same with or different from each other, a, b and c each is a number with $1.0 \leq a \leq 2.5$, $0.001 \leq b \leq 1.5$, and $0.001 \leq c \leq 1.5$, d, e and f each is an integer with $0 \leq d \leq 15$, $0 \leq e \leq 50$, and $0 \leq f \leq 50$, x is an integer with $1 \leq x \leq 5$, and y is an integer with $0 \leq y \leq 500$.

2. The method according to claim 1, wherein the organopolysiloxane of formula (1) has a weight average molecular weight of from 300 to 100,000.

3. The method according to claim 1 or 2, wherein $R^1$ is an alkyl group having 1 to 6 carbon atoms, a fluorinated alkyl group having 1 to 6 carbon atoms, or a group represented by the formula, —$C_3H_6O$-1-$(C_3H_6O)_fR^4$, wherein $R^4$ is an alkyl group having 7 to 30 carbon atoms and f is an integer with $0 \leq f \leq 50$, $R^2$ is an organic group represented by the following formula (4), $$\begin{array}{c} R^7_{3-p} \\ | \\ -C_zH_{2z}-Si-R^8_p \end{array} \quad (4)$$

wherein $R^7$ is a group selected from the group consisting of alkyl groups having 1 to 30 carbon atoms, alicyclic groups, aryl groups, aralkyl groups and fluorinated alkyl groups, $R^8$ is a hydroxyl group or an alkoxy group having 1 to 6 carbon atoms, z is an integer of from 1 to 5, and p is an integer of from 1 to 3, in the formula (3), $R^6$ is an alkyl group having 1 to 6 carbon atoms, x is 2, and y is an integer of from 1 to 15, and a, b and c each is a number with $1.2 \leq a \leq 2.3$, $0.05 \leq b \leq 1.0$, and $0.05 \leq c \leq 1.0$.

4. The method according to claim 1, wherein the method further comprises, prior to the step of application of the organopolysiloxane hair treatment composition, steps of:

applying to the hair a second composition comprising at least one selected from the group consisting of amino-modified silicones, amino acid-modified silicones, and carboxyl-modified silicones, and washing the hair with water.

5. A method of conditioning hair, said method comprising the sequential steps of:
applying to the hair a composition comprising at least one member selected from the group consisting of amino-modified silicones, amino acid-modified silicones, and carboxyl-modified silicones;
washing the hair with water;
applying to the hair an organopolysiloxane hair treatment composition which comprises an organopolysiloxane represented by the following formula (1), dispersed or dissolved in an organic solvent:

$$R^1{}_a R^2{}_b R^3{}_c SiO_{(4-a-b-c)/2} \quad (1)$$

wherein $R^1$ is an organic group selected from the group consisting of alkyl groups having 1 to 30 carbon atoms, alicyclic groups, aryl groups, aralkyl groups, fluorinated alkyl groups and an organic group represented by following formula (2), $$-C_dH_{2d}-O-(C_2H_4O)_e(C_3H_6O)_f R^4 \quad (2)$$

wherein $R^4$ is an alkyl group having 1 to 30 carbon atoms, provided that, when d=e=f=0, said alkyl group has 7 to 30 carbon atoms, or an organic group represented by the formula, $R^5$—(CO)—, wherein $R^5$ is an alkyl group having 1 to 30 carbon atoms, $R^2$ is a group having at least one hydroxyl group or alkoxy group having 1 to 6 carbon atoms, wherein said hydroxyl group or alkoxy group is bonded to a silicon atom in the formula (1) directly or via an alkylenesilyl group, $R^3$ is a silicone compound residue represented by the following formula (3),

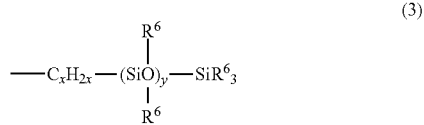

(3)

wherein $R^6$ is a group selected from the group consisting of alkyl groups having 1 to 30 carbon atoms, alicyclic groups, aryl groups, aralkyl groups, and fluorinated alkyl groups, wherein when two or more of the groups $R^1$, $R^2$, $R^3$, $R^4$, $R^5$ or $R^6$, respectively, are present in a molecule, such are the same with or different from each other, a, b and c each is a number with $1.0 \leq a \leq 2.5$, $0.001 \leq b \leq 1.5$, and $0.001 \leq c \leq 1.5$, d, e and f each is an integer with $0 \leq d \leq 15$, $0 \leq e \leq 50$, and $0 \leq f \leq 50$, x is an integer with $1 \leq x \leq 5$, and y is an integer with $0 \leq y \leq 500$; and, after the step of application of the organopolysiloxane hair treatment composition,
applying to the hair a composition comprising an amino-modified silicone.

6. The method according to claim 4 or 5, wherein the amino-modified silicone is at least one selected from the group consisting of silicones having an amino group grafted to a silicone backbone, silicones having an amino group bonded to either one end of a silicone backbone, silicones having amino groups bonded to both ends of a silicone backbone, silicones having amino groups bonded to both ends of a silicone backbone and an amino group grafted to the silicone backbone, and silicones having a silicone chain and an amino group both grafted to a silicone backbone.

7. The method according to claim 6, wherein the amino-modified silicone is represented by the following formula (6),

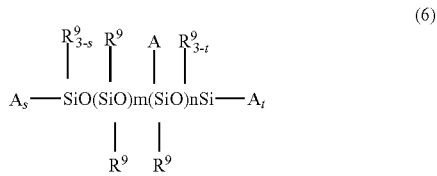

(6)

wherein A is —$R^{10}NH_2$ or —$R^{10}NHR^{11}NH_2$, wherein $R^{10}$ and $R^{11}$ are alkylene groups having 1 to 8 carbon atoms, $R^9$ is the same with or different from each other and is selected from the group consisting of alkyl groups having 1 to 30 carbon atoms, alicyclic groups, aryl groups, aralkyl groups, and fluorinated alkyl groups, m and n are the same with and different from each other and are integers of from 0 to 300, and s and t are the same with or different from each other and are integers of from 0 to 3 with $1 \leq n+s+t$.

8. The method according to claim 1, wherein said organopolysiloxane hair treatment composition is in the form of a liquid, milky lotion, cream, solid, paste, gel, multilayer, mousse, spray or stick.

9. The method according to claim 1, wherein said organopolysiloxane hair treatment composition consists essentially of an organic solvent and said organopolysiloxane dispersed or dissolved in said organic solvent.

* * * * *